US012797350B2

(12) United States Patent
Zheng et al.

(10) Patent No.: US 12,797,350 B2
(45) **Date of Patent: *Nov. 17, 2026**

(54) ORAL PHARMACEUTICAL IMMEDIATE RELEASE COMPOSITION AND METHOD OF TREATMENT FOR WEIGHT LOSS

(71) Applicant: AARDVARK THERAPEUTICS INC., San Diego, CA (US)

(72) Inventors: Zhenhuan Zheng, San Diego, CA (US); Tien-Li Lee, San Diego, CA (US)

(73) Assignee: Aardvark Therapeutics Inc., San Diego, CA (US)

( * ) Notice: Subject to any disclaimer, the term of this patent is extended or adjusted under 35 U.S.C. 154(b) by 1275 days.

This patent is subject to a terminal disclaimer.

(21) Appl. No.: 17/702,452

(22) Filed: Mar. 23, 2022

(65) Prior Publication Data

US 2022/0280457 A1 Sep. 8, 2022

Related U.S. Application Data

(63) Continuation of application No. PCT/US2020/052588, filed on Sep. 24, 2020.

(Continued)

(51) Int. Cl.

*A61K 31/167* (2006.01)
*A61K 9/16* (2006.01)

(Continued)

(52) U.S. Cl.

CPC .......... *A61K 31/167* (2013.01); *A61K 9/1652* (2013.01); *A61K 47/12* (2013.01); *A61P 3/04* (2018.01); *A61P 5/50* (2018.01)

(58) Field of Classification Search

CPC .................. A61P 3/04; A61P 5/50; A61P 1/00

See application file for complete search history.

(56) References Cited

U.S. PATENT DOCUMENTS 7,655,256 B2 2/2010 Hughes
7,939,671 B2 5/2011 Li et al.

(Continued)

FOREIGN PATENT DOCUMENTS

JP 2011-520880 A 7/2011
JP 2013-528661 A 7/2013

(Continued)

OTHER PUBLICATIONS

Avau et al., "Targeting extra-oral bitter taste receptors modulates gastrointestinal motility with effects on satiation," Scientific Reports, 5: 15985, 12 pages (2015).

(Continued)

*Primary Examiner* — Renee Claytor
*Assistant Examiner* — Andrew P Lee
(74) *Attorney, Agent, or Firm* — McNeill PLLC

(57) ABSTRACT

There is disclosed an oral pharmaceutical composition for the treatment of multiple diseases comprising a denatonium cation salt and a sour anion selected from the group consisting of acetate (DA), citrate (DC) tartrate (CT), maleate (DM) and combinations thereof (collectively "denatonium salt") and pharmaceutical excipients for gastric release of the denatonium salt. There is further disclosed an oral immediate release pharmaceutical composition to substantially release an API (active pharmaceutical ingredient) in the gastric area of the GI tract formulation, wherein the API comprises an effective amount of the denatonium salt. Preferably, the oral immediate release pharmaceutical formulation comprises from about 0.5 g to about 5 g of the denatonium salt delivering a daily dose of the denatonium salt from about 20 mg to about 150 mg to a human adult.

16 Claims, 7 Drawing Sheets

Related U.S. Application Data

(60) Provisional application No. 62/905,943, filed on Sep. 25, 2019.

(51) Int. Cl.

| | |
|---|---|
| ***A61K 47/12*** | (2006.01) |
| ***A61P 3/04*** | (2006.01) |
| ***A61P 5/50*** | (2006.01) |

(56) References Cited

U.S. PATENT DOCUMENTS

| | | | |
|---|---|---|---|
| 8,445,692 | B2 | 5/2013 | Karanewsky et al. |
| 8,796,233 | B2 | 8/2014 | Goddard, III et al. |
| 9,272,051 | B2 | 3/2016 | Goddard, III et al. |
| 10,330,678 | B2 | 6/2019 | Goddard, III et al. |
| 10,610,500 | B2 | 4/2020 | Baron et al. |
| 10,835,505 | B2 | 11/2020 | Lee |
| 2003/0198666 | A1 | 10/2003 | Abbas et al. |
| 2007/0104751 | A1 | 5/2007 | Levar |
| 2011/0091509 | A1 | 4/2011 | Howard et al. |
| 2014/0030332 | A1 | 1/2014 | Baron et al. |
| 2014/0302528 | A1 | 10/2014 | Li et al. |
| 2017/0066996 | A1 | 3/2017 | Labeque et al. |
| 2017/0067000 | A1 | 3/2017 | Brandt-Sanz et al. |
| 2017/0067002 | A1 | 3/2017 | Cumming |
| 2018/0161298 | A1 | 6/2018 | Deretic et al. |
| 2019/0038576 | A1 | 2/2019 | Baron et al. |
| 2019/0374489 | A1 | 12/2019 | Lee |
| 2022/0087960 | A1 | 3/2022 | Zheng et al. |

FOREIGN PATENT DOCUMENTS

| | | | |
|---|---|---|---|
| KR | 10-2004-0063616 | A | 7/2004 |
| WO | 2009/139888 | A1 | 11/2009 |
| WO | 2011/160093 | A2 | 12/2011 |
| WO | 2016/172479 | A1 | 10/2016 |
| WO | 2017/040560 | A1 | 3/2017 |
| WO | 2020/010166 | A1 | 1/2020 |
| WO | 2020/014494 | A1 | 1/2020 |

OTHER PUBLICATIONS

Avau et al., "The Gustatory Signaling Pathway and Bitter Taste Receptors Affect the Development of Obesity and Adipocyte Metabolism in Mice," PLoS One 10(12): e0145538, 18 pages (2015).
Deckmann et al., "Bitter triggers acetylcholine release from polymodal urethral chemosensory cells and bladder reflexes," PNAS, 111(22): 8287-8292 (2014).
Deloose et al., "Intragastric infusion of denatonium benzoate attenuates interdigestive gastric motility and hunger scores in healthy female volunteers," Am. J. Clin. Nutr., 105: 580-588 (2017).
Glendinning et al., "Intragastric infusion of denatonium conditions flavor aversions and delays gastric emptying in rodents," Physiol. Behav., 93(4-5): 757-765 (2008).
Grassin-Delyle et al., "The expression and relaxant effect of bitter taste receptors in human bronchi," Respiratory Research, 14:134, 14 pages (2013).
Hao et al., "Role of CCK1 and Y2 receptors in activation of hindbrain neurons induced by intragastric administration of bitter taste receptor ligands," Am. J. Physiol. Regul. Integr. Comp. Physiol. 294: R33-R38 (2008).
Janssen et al., "Bitter taste receptors and α-gustducin regulate the secretion of ghrelin with functional effects on food intake and gastric emptying," PNAS, 108(5): 2094-2099 (2011).
Kim et al., "Denatonium induces secretion of glucagon-like peptide-1 through activation of bitter taste receptor pathways," Diabetologia, 57: 2117-2125 (2014).
Manson, "Bitter taste receptor agonists mediate relaxation of human and rodent vascular smooth muscle," Eur. J. Pharmacol., 740: 302-311 (2014).
Meyerhof et al., "The Molecular Receptive Ranges of Human TAS2R Bitter Taste Receptors," Chem. Senses, 35: 157-170 (2010).
Miyata et al., "Effect of five taste ligands on the release of CCK from an enteroendocrine cell line, STC-1," Biomedical Research (Tokyo), 35(2): 171-176 (2014).
Peters et al., "The effect of two weeks ingestion of a bitter tastant mixture on energy intake in overweight females," Appetite, 107: 268-273 (2016).
Pulkkinen et al., "The bitter taste receptor (TAS2R) agonists denatonium and chloroquine display distinct patterns of relaxation of the guinea pig trachea," Am. J. Physiol. Lung Cell Mol. Physiol., 303: L956-L966 (2012).
Sai et al., "Bitter tastants induce relaxation of rat thoracic aorta precontracted with high K+," Clin. Exp. Pharmacol. Physiol., 41: 301-308 (2014).
Schier et al., "Ongoing ingestive behavior is rapidly suppressed by a preabsorptive, intestinal 'bitter taste' cue," Am. J. Physiol. Regul. Integr. Comp. Physiol., 301: R1557-R1568 (2011).
Straub et al., "Stimulation of Insulin Secretion by Denatonium, One of the Most Bitter-Tasting Substances Known," Diabetes, 52: 356-364 (2003).
Upadhyaya et al., "Dextromethorphan Mediated Bitter Taste Receptor Activation in the Pulmonary Circuit Causes Vasoconstriction," PLOS One 9(10): e110373, 12 pages (2014).
Zhai et al., "Activation of bitter taste receptors (tas2rs) relaxes detrusor smooth muscle and suppresses overactive bladder symptoms," Oncotarget, 7(16): 21156-21167 (2016).
Copenheaver, International Search Report for PCT App. No. PCT/US2020/052588, mailed Jan. 28, 2021, 3 pages.
Copenheaver, Written Opinion of the International Searching Authority for PCT App. No. PCT/US2020/052588, mailed Jan. 28, 2021, 6 pages.
Neithammer et al., "First-in-Human Evaluation of Oral Denatonium Acetate (ARD-101), a Potential Bitter Taste Receptor Agonist: A Randomized, Double-Blind, Placebo-Controlled Phase 1 Trial in Healthy Adults," Clin. Pharm. Drug Dev., 11(8): 997-1006 (2022).
Aardvark Therapeutics, Inc. (responsible party), "Study to Evaluate ARD-101 in Adults with Obesity," from ClinicalTrials.gov, ID NCT05121441, available at https://www.clinicaltrials.gov/study/NCT05121441?titles=Study%20to%20Evaluate%20ARD-101%20in%20Adults%20With%20Obesity&rank=1, 13 pages, last update posted Jan. 13, 2023.

| Manufacturing Step | Material | Equipment and Process |
|---|---|---|
| **Drug Layering Process** | - Denatonium Acetate<br>- Povidone USP (KOLLIDON 30)<br>- Ethyl Alcohol USP 190 Proof (190 Proof Ethyl Alcohol)<br>- Sugar Spheres NF, (VIVAPHARM® Sugar Spheres 35-45) | Equipment: VFC LAB-3 equipped with GXR-35 insert<br>Process: Drug solution is prepared by dissolving Povidone and Denatonium Acetate in ethyl alcohol. Drug solution is layered onto sugar spheres in the rotor granulator. |
| **Screening** | Denatonium drug layered pellets | Equipment: mesh #20<br>Process: Drug layered pellets are screened through mesh #20 hand sieve to remove any agglomerates |
| **Seal Coating Process** | -Denatonium Drug layered pellets<br>-Hypromellose USP (Methocel E5 Premium LV Hydroxypropyl Methylcellulose)<br>-Talc USP (MicroTalc MP 1538 USP Talc)<br>-Ethyl Alcohol USP 190 Proof (190 Proof Ethyl Alcohol)<br>-Purified Water USP | Equipment: VFC LAB-3 equipped with GXR-35 insert<br><br>Process: Seal coating dispersion is prepared by dissolving Hypromellose in a mixture of ethyl alcohol and water, followed by dispersing talc. Seal coating dispersion is layered onto Denatonium Drug layered pellets in the rotor granulator. |
| **Screening** | Denatonium drug seal coated pellets | Equipment: mesh #20<br>Process: Denatonium Seal Coated Pellets are screened through mesh #20 hand sieve to remove any agglomerates |
| **Final Blending** | - Denatonium Seal Coated Pellets<br>- Talc USP (MicroTalc MP 1538 USP Talc) | Equipment: mesh #60,<br>V-Blender – 4 qt shell<br>Process: Talc is screened through mesh #60 hand sieve to remove any agglomerates and blended with Denatonium Seal coated pellets for 10 minutes. |

FIG. 8

ORAL PHARMACEUTICAL IMMEDIATE RELEASE COMPOSITION AND METHOD OF TREATMENT FOR WEIGHT LOSS

RELATED APPLICATIONS

This application is a continuation of International Patent Application No. PCT/US2020/052588, filed Sep. 24, 2020, which claims the benefit of priority to U.S. Provisional Application No. 62/905,943, filed on Sep. 25, 2019, the entire contents of each of which are expressly incorporated herein by reference.

TECHNICAL FIELD

The present disclosure provides an oral pharmaceutical composition for the treatment of multiple diseases comprising a denatonium cation salt and a sour anion selected from the group consisting of acetate (DA), citrate (DC) tartrate (CT), maleate (DM) and combinations thereof (collectively "denatonium salt") and pharmaceutical excipients for gastric release of the denatonium salt. The present disclosure further provides an oral immediate release pharmaceutical composition to substantially release an API (active pharmaceutical ingredient) in the gastric area of the GI tract formulation, wherein the API comprises an effective amount of the denatonium salt. Preferably, the oral immediate release pharmaceutical formulation comprises from about 0.5 g to about 5 g of the denatonium salt delivering a daily dose of the denatonium salt from about 20 mg to about 150 mg to a human adult.

BACKGROUND

Chemosensory signaling of nutrients plays a role in regulating appetite, digestion, and metabolism. In particular, a variety of bitter taste receptors (TAS2R) family of G-protein-coupled receptors (GPCRs) exist not only in the oral cavity, but on gut endocrine cells, human gastric smooth muscle cells, adipocytes, as well as sites in the chemoreceptor trigger zone in the medulla of the brain.

Obesity is a global pandemic that has led to serious health and socioeconomic consequences for millions of adults and children (Bluher, *Nat. Rev. Endocrinol.* 15 (2019) 288-298). Globally, at least 13% of adults and 7% of children are obese, but in several countries the prevalence of obesity is at least 30% of the overall population (Ng et al. *Lancet* 384 (2014) 766-781).

Obesity is ideally treated with dieting and physical exercise, but success rates for such programs have been observed to be low, at approximately 20%. Often, this is largely due to a strong appetite drive. which has redundant stimulatory pathways. and is difficult to overcome, as suppression of one pathway for appetite generation frequently results in upregulation of compensatory alternate pathways to invoke hunger over time. Various medications that have been commercially available confer generally modest results or have accompanying risk and side effects that are deemed intolerable by many, or both.

Anorexigenic stimulant compounds such as ephedrine, fenfluramine, and dexfenfluramine were withdrawn from the market due to associated cardiovascular safety risks. Drugs that interfere with nutrient absorption such as Orlistat, a lipase inhibitor, which blocks fat processing in the gut, results in oily stool and diarrhea. Central nervous system targeted drugs such as Sibutramine (a monoamine oxidase inhibitor), Rimonabant (a cannabinoid receptor antagonist), and others, have significant central nervous system (CNS) "off-target" effects often leading to unintended psychiatric or neurological manifestations.

Behavioral interventions for obesity, such as exercise regimens and changes in diet, often fail, and bariatric surgery is not an option for most people. Anti-obesity drugs can be effective at lowering body weight; however, they have been associated with side effects ranging from headache, nausea, and dizziness to severe psychiatric and cardiovascular events (M. O. Dietrich et al., *Nat. Rev. Drug Discov.* 11 (2012) 675-691). Given the enormous medical, societal, and economic burden of obesity, there is an urgent need to develop novel, safe, and effective therapeutic agents for this debilitating and potentially fatal disease.

Bitter taste receptors (TAS2Rs) comprise a family of several G-protein coupled receptors (GPCRs) that are expressed on the tongue as well as other organs, including the brain, oral cavity, lung, pancreas, and gastrointestinal mucosa (Jaggupilli et al., *Mol. Cell. Biochem.* 426 (2017) 137-147).

Denatonium benzoate activates to varying degrees eight human TAS2Rs (TAS2R 4, 8, 10, 13, 39, 43, 46, and 47) (Meyerhof et al., Chem. Senses 35 (2010) 157-170). In rodent obesity models, the benzoate salt of denatonium suppressed food intake and inhibited weight gain (Avau et al., *PLoS One* 10 (2015) e0145538; and Glendinning et al., *Physiol. Behav.* 93 (2008) 757-765). Further, in healthy volunteers, denatonium benzoate attenuated inter-digestive gastric motility, reduced nutrient volume tolerance, decreased hunger ratings, and increased satiation post meal after intragastric administration (Avau et al., *Sci. Rep.* 5 (2015) 15985; and Deloose et al., *Am. J. Clin. Nutr.* 105 (2017) 580-588). However, a significant side effect problem emerged with the two denatonium benzoate studies due to the aversive nature of denatonium benzoate. Therefore, there is a significant need in the art to address obesity and related disorders with an improved bitter agonist that has a safer profile. The present disclosure addresses this need.

SUMMARY

The present disclosure is based on a finding that denatonium salts that have a sour anion have better side effect profiles seen in comparative in vivo studies versus denatonium benzoate, the only available denatonium salt and the denatonium salt reported in earlier studies.

The present disclosure provides an oral pharmaceutical composition for the treatment of multiple diseases comprising a denatonium cation salt and a sour anion selected from the group consisting of acetate (DA), citrate (DC) tartrate (CT), maleate (DM) and combinations thereof (collectively "denatonium salt") and pharmaceutical excipients for gastric release of the denatonium salt. The present disclosure further provides an oral immediate release pharmaceutical composition to substantially release an API (active pharmaceutical ingredient) in the gastric area of the GI tract formulation, wherein the API comprises an effective amount of the denatonium salt. Preferably, the oral immediate release pharmaceutical formulation comprises from about 0.5 g to about 5 g of the denatonium salt delivering a daily dose of the denatonium salt from about 20 mg to about 150 mg to a human adult.

The present disclosure provides an oral pharmaceutical immediate gastric release pharmaceutical formulation ("oral formulation") comprising granules which comprise a denatonium cation salt and a sour anion selected from the group consisting of acetate (DA), citrate (DC) tartrate (CT), maleate (DM) and combinations thereof (collectively "denatonium salt") and pharmaceutical excipients for gastric release of the denatonium salt. Preferably the pharmaceutical excipients comprise talc, a cellulose and a saccharide. Preferably, the oral formulation further comprises an organic acid selected from the group consisting of acetic acid, malic acid, maleic acid, citric acid and combinations thereof. Preferably, the oral formulation further comprises from about 0.5 g to about 5 g acetic acid. More preferably, the dosage per day of the acetic acid for an adult is from about 1.5 g to about 3 g. Preferably the daily dosage of DA for an adult is from about 10 mg to about 600 mg or from about 5 mg/kg to about 50 mg/kg body weight per day. More preferably, the daily dosage of DA for an adult is from about 10 mg to about 200 mg. Most preferably, the daily dosage of DA for an adult is from about 10 mg to about 100 mg, or to achieve a concentration in the GI tract of from about 10 parts per billion to about 10 ppm. In view of the sustained release or immediate release characteristics, the daily dose of DA is once per day, twice per day or three times per day.

Further, the present disclosure provides a sustained release oral formulation comprising DA and acetic acid powder in a sustained release cellulosic and mannitol excipient formulation. Preferably the daily dosage of DA for an adult is from about 10 mg to about 600 mg. More preferably, the daily dosage of DA for an adult is from about 10 mg to about 200 mg. Most preferably, the daily dosage of DA for an adult is from about 10 mg to about 100 mg, or to achieve a concentration in the GI tract of from about 10 parts per billion to about 10 ppm. Preferably, the oral formulation comprises from about 0.01% to about 10 wt % DA and from about 10% to about 90 wt % dry acetic acid powder. Preferably, the dose administered of DA is from about 500 nmol/kg to about 4 μmol/kg. Preferably, the dose administered of DA is from about 10 mg to about 50 mg for an adult. In view of the release characteristics, the daily dose of DA is once per day, twice per day or three times per day.

The present disclosure further provides a method for effecting weight loss, comprising administering an oral pharmaceutical immediate gastric release pharmaceutical formulation ("oral formulation") comprising granules which comprise a denatonium cation salt and a sour anion selected from the group consisting of acetate (DA), citrate (DC) tartrate (CT), maleate (DM) and combinations thereof (collectively "denatonium salt") and pharmaceutical excipients for gastric release of the denatonium salt. Preferably the pharmaceutical excipients comprise talc, a cellulose and a saccharide. Preferably, the oral formulation further comprises an organic acid selected from the group consisting of acetic acid, malic acid, maleic acid, citric acid and combinations thereof. Preferably, the oral formulation further comprises from about 0.5 g to about 5 g acetic acid. More preferably, the dosage per day of the acetic acid for an adult is from about 1.5 g to about 3 g. Preferably, the daily dosage of DA for an adult is from about 10 mg to about 600 mg or from about 5 mg/kg to about 50 mg/kg body weight per day. More preferably, the daily dosage of DA for an adult is from about 10 mg to about 200 mg. Most preferably, the daily dosage of DA for an adult is from about 10 mg to about 100 mg, or to achieve a concentration in the GI tract of from about 10 parts per billion to about 10 ppm.

FIGURES

DETAILED DESCRIPTION

Figure 1:
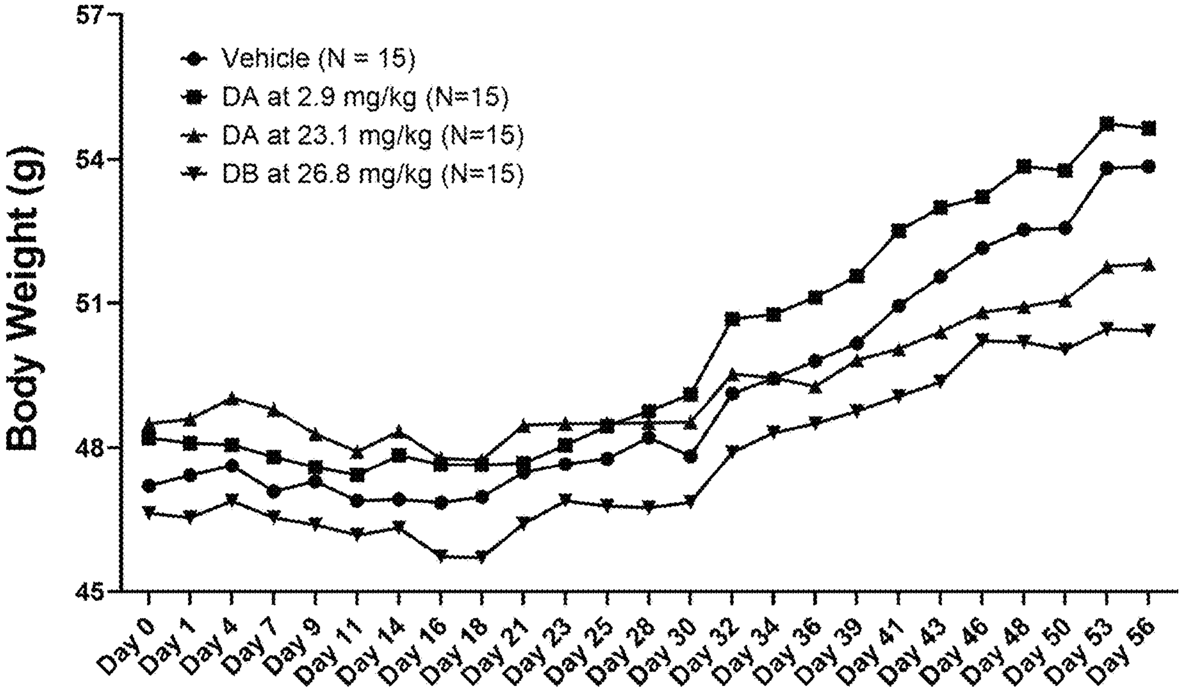
FIG. 1 shows a 56 day DIO mouse weight loss study comparison (Example 3) of body weights at the indicated days. The higher dose DA group (23.1 mg/kg) showed the lowest average body weights.
Figure 2:
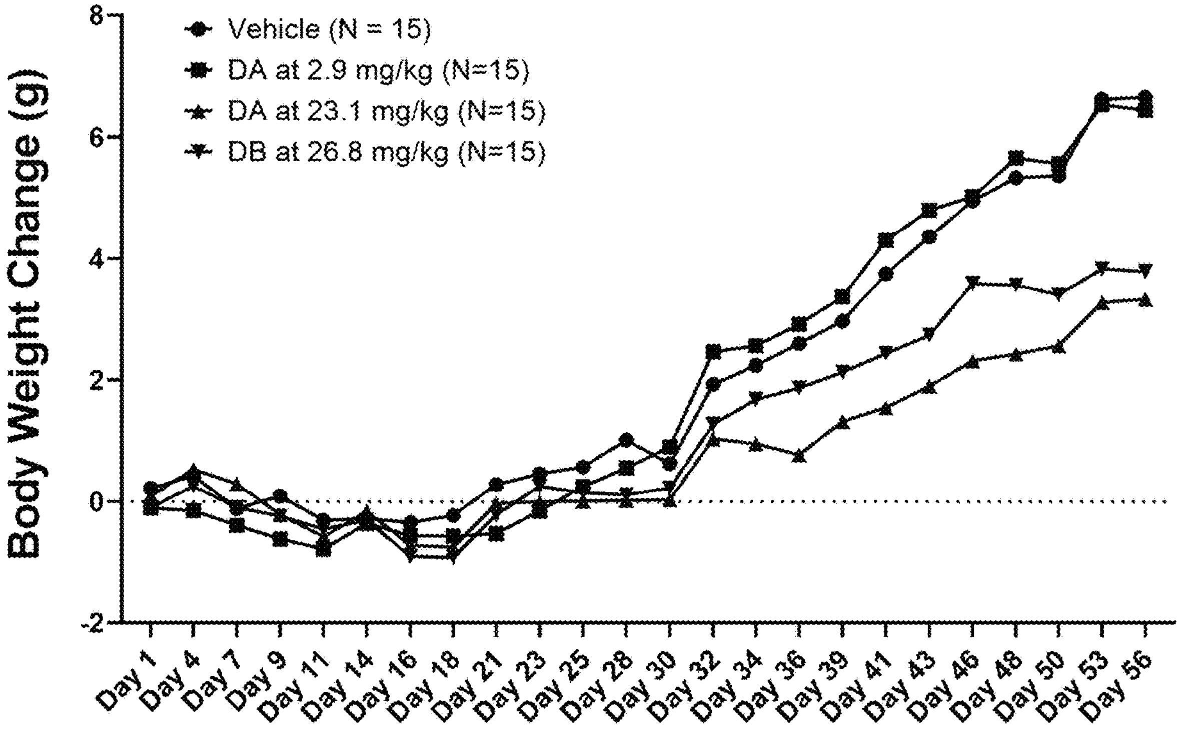
FIG. 2 shows the results of body weight changes of the 56 day study in Example 3. Animals treated with 23.1 mg/kg DA showed the lowest increase in body weight over a higher dose DB group.
Figure 3:
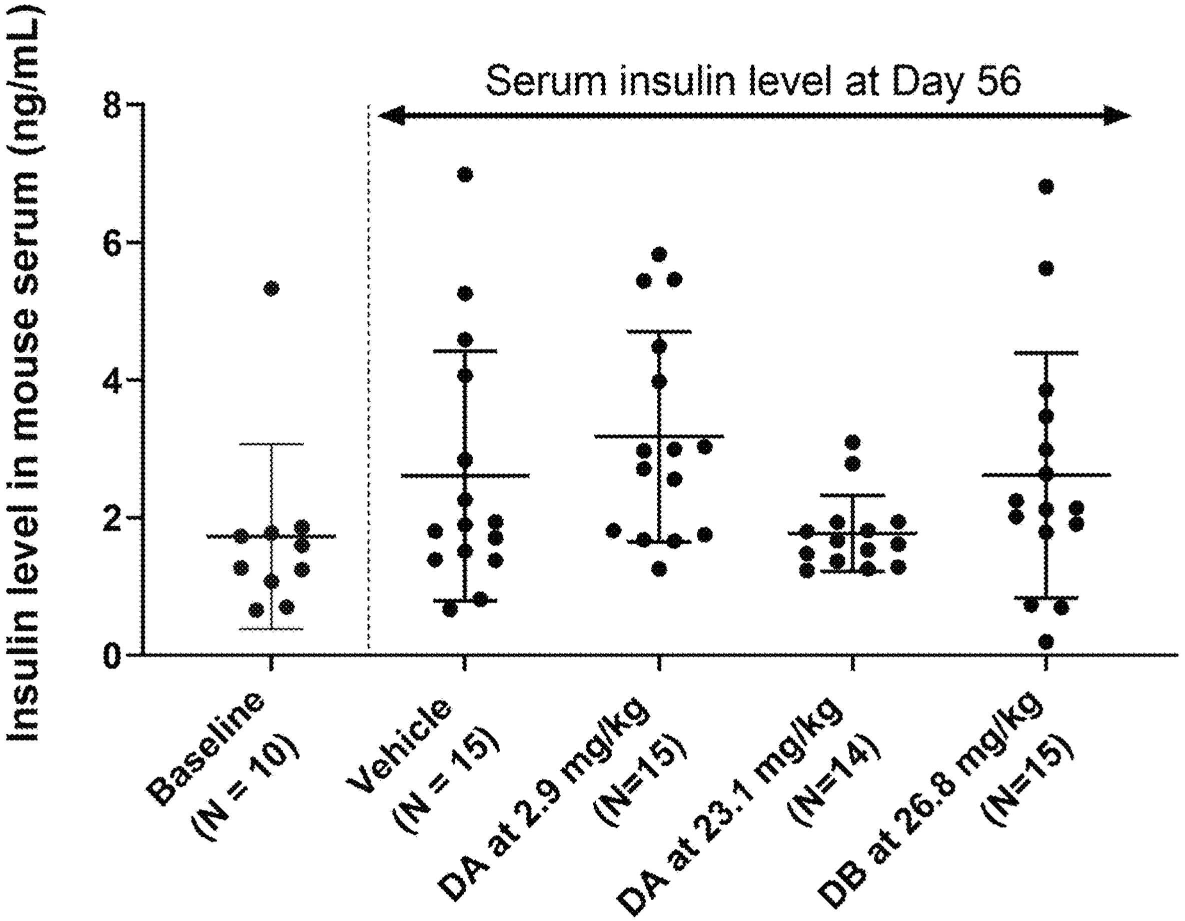
FIG. 3 shows the results of serum insulin at the end of the 56 day study in Example 3. Serum insulin in the 23.1 mg/kg DA group was close to baseline value (i.e., pre-treatment) and noticeably lower compared to the vehicle-treated group.
Figure 4:
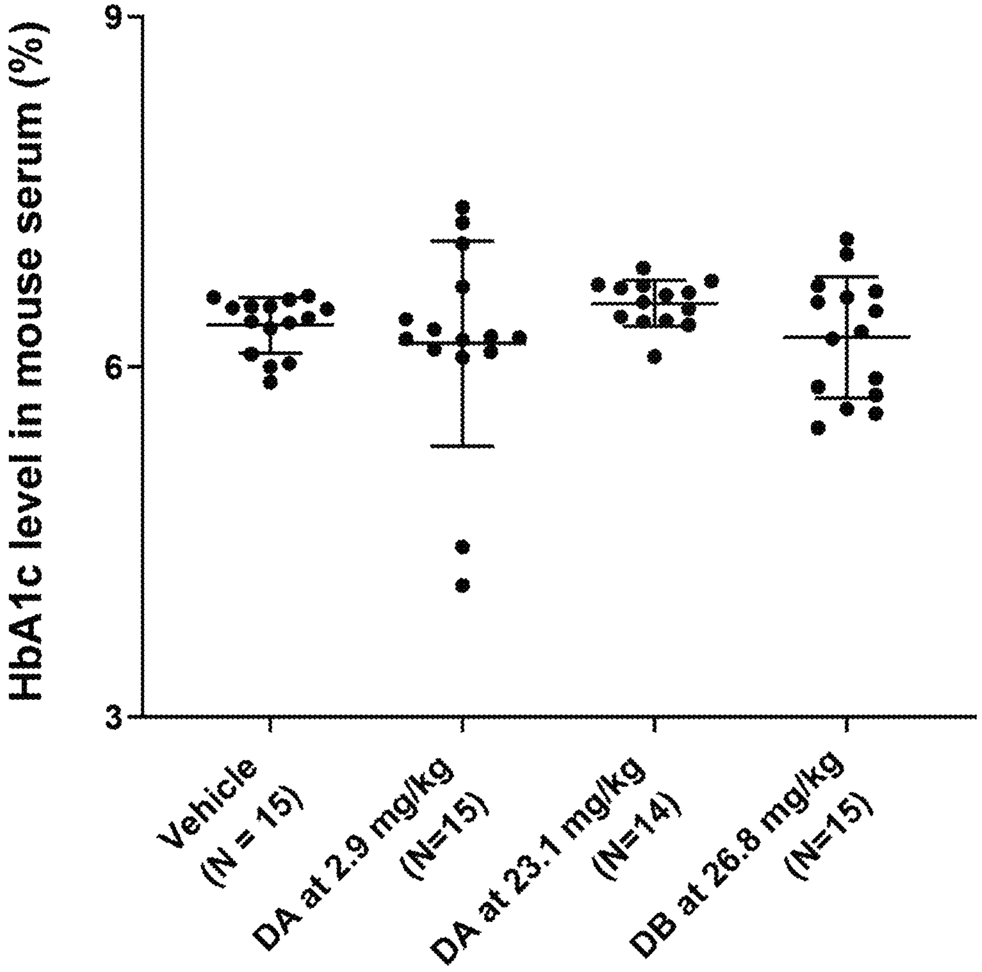
FIG. 4 shows that there was no statistical difference in serum HBA1c levels among all the experimental groups in Example 3.

The present disclosure is based on a surprising finding that the anti-obesity effects of denatonium salts are superior (both safety and efficacy) with a sour-tasting anion (acetate, citrate, tartrate and maleate) using in vitro and in vivo models of obesity. The objectives of our study were to determine the effects of denatonium salts with a sour-tasting anion on food and water consumption, body weight control.

In a short-term food intake inhibition study, in Sprague Dawley rats the doses of DA administered are 7.5, 15, 30, and 60 μmol/kg. The corresponding human equivalent doses (HED) are 1.2, 2.4, 4.9, 9.7 μmol/kg, respectively. In a longer-term food intake inhibition study in C57BL/6NTac mice the dose of DA is 60 μmol/kg. The corresponding HED is 4.9 μmol/kg. As a background, according to Avau et al. (*Sci. Rep.* (2015) 5:15985), oral administration of only denatonium benzoate (DB), a related salt to DA, at 60 μmol/kg (26.8 mg/kg) significantly inhibited gastric emptying rate in normal C57BL/6 mice. In another study, treatment with 60 μmol/kg DB (26.8 mg/kg) once daily induced a decrease in body weight of C57BL/6 DIO mice during a 28-day period, as compared to vehicle. According to Avau et al., healthy volunteers receiving 1 μmol/kg DB showed decreased nutrient volume tolerance and increased satiation. Therefore, the disclosed formulation provides a dose of DA from about 500 nmol/kg to about 10 μmol/kg, which corresponds to from about 10 mg to about 230 mg for a human adult.

TABLE 1

| Denatonium salts | |
|---|---|
| name | chemical structure |
| Denatonium benzoate (DB) | 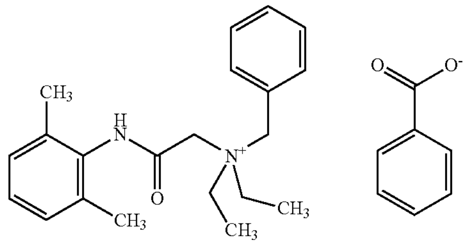 [SMILES: CC[N+](CC)(CC(=O)Nc1c(C)cccc1C)Cc1ccccc1 ; O=C([O-])c1ccccc1] |

TABLE 1-continued

| Denatonium salts | |
|---|---|
| name | chemical structure |
| Denatonium acetate | 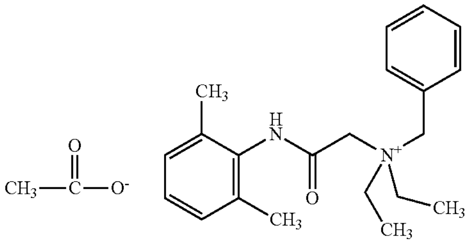 |

Denatonium Benzoate (DB)

IUPAC Name: benzyl-[2-(2,6-dimethylanilino)-2-oxoethyl]-diethylazanium benzoate

Molecular Formula: $C_{28}H_{34}N_2O_3$

Molecular Mass: 446.581 g/mol

CAS Number: 3734-33-6

ChemSpider ID:

Denatonium, usually available as denatonium benzoate (under trade names such as BITTERANT-b, BITTER+PLUS, Bitrex or Aversion). It is used as an aversive agent (bitterants) to prevent inappropriate ingestion. Denatonium benzoate is used in denatured alcohol, antifreeze, nail biting preventions, respirator mask fit-testing, animal repellents, liquid soaps, and shampoos. It is not known to pose any long-term health risks.

A treatment that could utilize a compound with low inherent toxicity to trigger extra-oral bitter receptors in the gut, brain, and other regions such as adipocytes provides a relatively safe means to decrease appetite and increase satiety selectively without the "off-target" CNS effects or GI disturbance typical of other obesity medications.

A clinical use for a combination orally ingested tablet or pill containing DA in combination with an organic acid, such as acetic acid, beyond obesity is Prader-Willi Syndrome. Among the key hallmarks of this genetic disorder is a constant hunger drive and a lack of sense of satiety even after eating copious amounts of food. Therefore, the present disclosure provides a method for treating Prader-Willi Syndrome (PWS) comprising an anti-obesity oral formulation comprising (a) denatonium acetate (DA), (b) an organic acid selected from the group consisting of acetic acid, malic acid, maleic acid, citric acid and combinations thereof; and (c) pharmaceutical excipients to facilitate a sustained release during transit through the GI tract.

EXAMPLE 1

This example describes a method for formulating a Denatonium Acetate/Acetic Acid Release Tablet, 44.6 mg/500 mg.

TABLE 2

| Ingredient | Per dose[1], mg | Quantity, kg |
|---|---|---|
| Denatonium Acetate | 44.6 | 5.575 |
| Acetic Acid, NF (36.5% w/w) | 1370 | 171.25 |
| Microcrystalline Cellulose | 100 | 12.5 |
| Mannitol | 80 | 10 |
| Polyvinyl Pyrrolidone 30 (PVP 30) | 38 | 4.75 |
| Magnesium Stearate | 4 | 0.5 |
| Ethylcellulose aqueous dispersion (Aquacoat ECD 30, FMC). | 786.7 | 98.34 |
| Dibutyl Sebacate | 59 | 7.375 |

[1]A dose can be from one to five tablets

Add microcrystalline cellulose (Avicel PH101), denatonium acetate, PVP 30 (half quantity) and mannitol to a 10 cubic feet V-blender and mix for 10 minutes. Transfer the blend to a high shear granulator and start granulating with a controlled spray rate of acetic acid (half quantity) at 800 g/minute. After granulation, the wet granules are removed and placed in a tray dryer controlled at 50° C. for a period until the final moisture content is below 2% w/w. The dried granules are subsequently passed through a Fitzmill equipped with 18 mesh screen. The milled granules are then placed back to the same high shear granulator and add the remaining half of the PVP 30 and again granulating with the remaining half of the acetic acid. The wet granules are removed and dried at 50° C. until the moisture content is below 2%. The dried granules are milled in a Fitzmill with 18 mesh screen, and then mixed with Magnesium Stearate in a 10 cubic feet V-blender for 5 minutes and the final blends are compressed in a tablet press with target 786.6 mg weight and 10 kp hardness (Uncoated Tablets).

The coating solution is prepared by dispersing dibutyl sebacate in the Aquacoat ECD 30 dispersion and gently mix for 1 hour. The Uncoated Tablets are loaded in a pan coater and sprayed with the Coating Solution at a controlled spray rate of 80 g/min. Continue drying for 30 minutes after the coating is complete.

EXAMPLE 2

This example describes a method of Denatonium Acetate/Acetic Acid Immediate Release Tablet, 22.3 mg/250 mg.

TABLE 3

| Ingredient | Per dose[2], mg | Quantity, kg |
|---|---|---|
| Denatonium Acetate | 22.3 | 4.46 |
| Acetic Acid, NF (36.5% w/w) | 685 | 137 |
| Microcrystalline Cellulose | 100 | 20 |
| Mannitol | 90.2 | 18.04 |
| Polyvinyl Pyrollidone 30 (PVP 30) | 25 | 5 |
| Magnesium Stearate | 2.5 | 0.5 |

[2]A dose can be from one to five tablets

Add microcrystalline cellulose (Avicel PH101), denatonium acetate, PVP 30 (half quantity) and mannitol to a 10 cubic feet V-blender and mix for 10 minutes. Transfer the blend to a high shear granulator and start granulating with a controlled spray rate of acetic acid (half quantity) at 800 g/minute. After granulation, the wet granules are removed and placed in a tray dryer controlled at 50° C. for a period until the final moisture content is below 2% w/w. The dried granules are subsequently passed through a Fitzmill equipped with an 18 mesh screen. The milled granules are then placed back to the same high shear granulator and add the remaining half of the PVP 30 and again granulating with the remaining half of the acetic acid. The wet granules are removed and dried at 50° C. until the moisture content is below 2%. The dried granules are milled in a Fitzmill with 18 mesh screen and then mixed with Magnesium Stearate in a 10 cubic feet V-blender for 5 minutes and the final blends are compressed in a tablet press with target 500 mg weight and 10 kp hardness.

EXAMPLE 3

This example shows an acute and a chronic in vivo study comparing the weight loss properties of DA versus DB (denatonium benzoate), two salts having the same cation and different anions. The 56-day study determined the behavioral effects of bitter taste receptor agonists denatonium acetate (DA) compared to denatonium benzoate (DB) in a diet-induced obesity (DIO) mouse model. The animals were acclimated in a vivarium for at least 3 days, maintained on a standard chow diet, 12:12 light/dark cycle and group housed 2-3 in heap-filtered cages. The study duration was a 3-5 day acclimation period +28 day study period and 2-3 day testing period after study. There were two DA dosages of 2.9 and 23.1 mg/kg BID (3.1 and 60 μmol/kg BID), 26.8 mg/kg DB BID and distilled water control vehicle with DA and DB made up in distilled water. The mice were C57BL/6NTad mice at least 12 weeks in age and 15 mice per group (low dose DA, higher dose DA, high dose DB and control). There were gross observations each day, and body weight measurements for each animal on Days 0, 1, 4, 7, 9, 11, 14, 16, 18, 21, 23, 25, 28, 30, 32, 34, 36, 39, 41, 43, 46, 48, 50, 53, and 56. Food intake was measured on Days 0, 7, 14, 21, 28, 35, 42, 49, and 56. Metabolic biomarkers (blood glucose, blood insulin, blood HbA1c) were measured at the beginning and end of the study. The DA, DB or distilled water control was administered per ostium gavage (PO) at a volume of 5 mL/kg body weight.

The results are shown in FIGS. 1-4 showing weight loss improvement of higher dose DA over higher dose DB.

EXAMPLE 4

Figure 5:
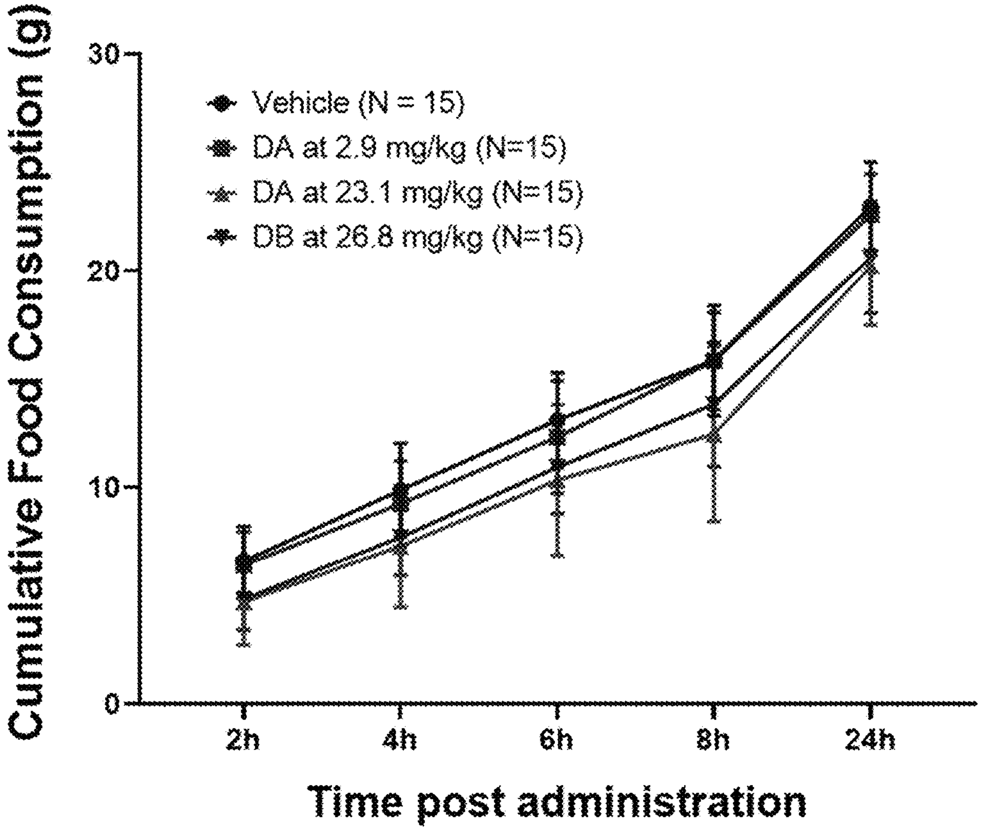
FIG. 5 shows cumulative food consumption over 24 hours for the single day rat study described in Example 4.

This example provides a 24 hour study comparing DA to DB is rats (male Sprague Dawley, Charles River) over a 24 hour period. The 5 groups of 15 rats each were vehicle controlled distilled water gavage QID, DB at a dose of 26.8 mg/kg gavage QID, DA low dose 2.9 mg/kg gavage QD, and DA high dose 23.1 mg/kg gavage QD. Food intake at 2 hr, 4 hr, 6 hr, 8 hr and 24 hr after administration was measured. The results of cumulative food consumption over 24 hour time are shown in FIG. 5 are that there was a significant main effect of drug treatment on cumulative food consumption with higher dose DA group having the largest impact.

EXAMPLE 5

This example describes the synthesis of denatonium acetate (DA).

Step 1: Synthesis of Denatonium Hydroxide from Lidocaine

To a reflux apparatus add 25 g of lidocaine, 60 ml of water and 17.5 g of benzyl chloride with stirring and heating in 70-90° C. The solution needs to be heated and stirred in the before given value for 24 h, the solution needs to be cooled down to 30° C. The unreacted reagents are removed with 3x10 mL of toluene. With stirring dissolve 65 g of sodium hydroxide into 65 mL of cold water and add it to the aqueous solution with stirring over the course of 3 h. Filter the mixture, wash with some water and dry in open air. Recrystallize in hot chloroform or hot ethanol.

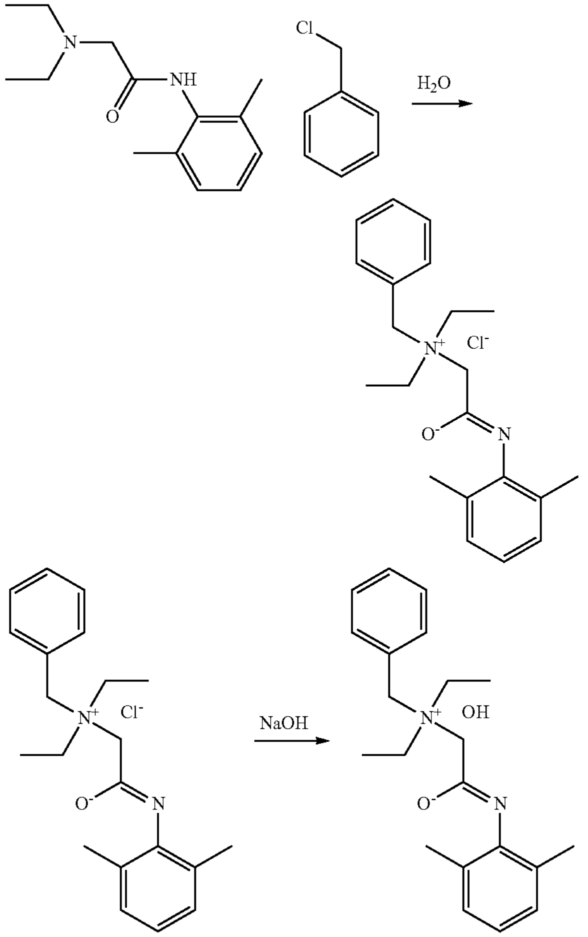

Step 2: Preparation of Denatonium Acetate from Denatonium Hydroxide

To a reflux apparatus 10 g of denatonium hydroxide (MW: 342.475 g/mol, 0.029 mol), 20 mL of acetone, and 2 g of acetic acid glacial (0.033 mol) dissolved in 15 mL of acetone is added, the mixture is stirred and heated to 35° C. for 3 h. Then evaporated to dryness and recrystallized in hot acetone.

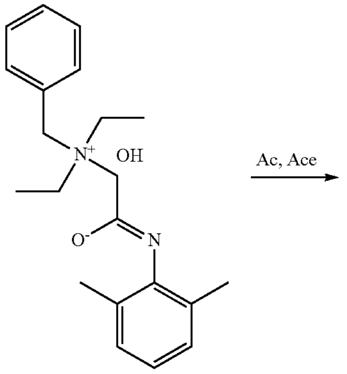

-continued

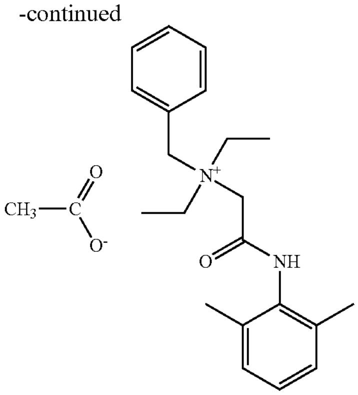

EXAMPLE 6

This example compares efficacy of DA versus DB in food inhibition and body weight control. As a background, according to Avau et al., Sci. Rep. (2015) 5:15985, oral administration of 26.8 mg/kg of DB significantly inhibited gastric emptying rate in normal C57BL/6 mice. In our first in vivo study, 45 male SD rats (purchased from Envigo at 8-10 weeks of age) were divided into three groups (15 in each group), which were administered a single oral dose of vehicle (distilled water), 26.8 mg/kg of DB, or 23.1 mg/kg of DA respectively, with a 24-hour observational period, to compare the efficacy of DB versus DA in reducing food intake.

TABLE 4

Mean cumulative food intake during 24-h observational period

| Group | Mean cumulative food intake (gram) 0-2 h | 0-4 h | 0-6 h | 0-8 h | 0-24 h |
|---|---|---|---|---|---|
| DA 23.1 mg/kg (N = 15) | 4.7 | 7.3 | 10.3 | 12.5 | 20.2 |
| DB 26.8 mg/kg (N = 15) | 4.8 | 7.7 | 10.9 | 13.8 | 20.6 |
| Vehicle (N = 15) | 6.6 | 9.9 | 13.1 | 15.9 | 23.0 |

The mean cumulative food intake during 24-h observational period is presented in Table 4. Administration with DB or DA reduced cumulative food intake during all the indicated time intervals as compared with vehicle. Additionally, a greater food intake reduction was observed with dosing with 23.1 mg/kg of DA than with 26.8 mg/kg of DB, although the molar dose of DA was even lower than DB (57.4 μmol/kg vs. 60 μmol/kg). Therefore, these data show that DA has a stronger efficacy than DB in food intake reduction on the basis of a different anion for the salt.

In another published article, treatment with 26.8 mg/kg of DB once daily induced a decrease in body weight of C57BL/6 diet-induced obese (DIO) mice during a 28-day period, as compared to vehicle (Avau et al. 2, *PLoS One.* 2015; 10 (12):e0145538). In a second in vivo study, 45 male C57BL/6N DIO mice (purchased from Envigo at 18 weeks of age, fed with high-fat diet) were divided into three groups (15 in each group), which were orally administered vehicle (distilled water), 26.8 mg/kg of DB, or 23.1 mg/kg of DA respectively, twice daily (BID), with a 56-day treatment period to compare the efficacy of DB versus DA in food intake reduction and body weight control. Briefly, once weekly, the food weight for each cage was recorded at 0 hour and then 24 hours later, permitting calculation of food consumption for that 24-hour interval. In addition, starting from Day 0, the mice were weighed three times weekly (every 2-3 days).

The mean food consumption per animal for 24-hour intervals at indicated measurement days during the treatment period are shown in Table. Notably, mice dosed with 23.1 mg/kg DA exhibited nominally decreased food consumption compared to vehicle-dosed mice; this effect was seen throughout the study. Lower food consumption was also seen on Days 0, 7, 28, 35, 42 and 49 in animals dosed with 26.8 mg/kg DB (compared to mice dosed with vehicle), but this was not the case on Days 14, 21, and 56. And on all indicated measurement days except for Day 42, food consumption was less in animals treated with 23.1 mg/kg of DA than in those treated with 26.8 mg/kg of DB.

TABLE 5

Mean food consumption per animal for 24-h interval at indicated measurement days

| Group | Mean food consumption per animal for 24-h interval (gram) Day 0 | Day 7 | Day 14 | Day 21 | Day 28 | Day 35 | Day 42 | Day 49 | Day 56 |
|---|---|---|---|---|---|---|---|---|---|
| DA 23.1 mg/kg | 2.2 | 1.7 | 1.9 | 2.3 | 2.0 | 2.4 | 2.0 | 2.3 | 1.7 |
| DB 26.8 mg/kg | 2.5 | 1.8 | 2.6 | 2.9 | 2.5 | 2.5 | 2.0 | 2.4 | 2.5 |
| Vehicle | 2.6 | 2.2 | 2.6 | 2.9 | 2.7 | 2.9 | 2.7 | 3.2 | 2.5 |

Figure 6:
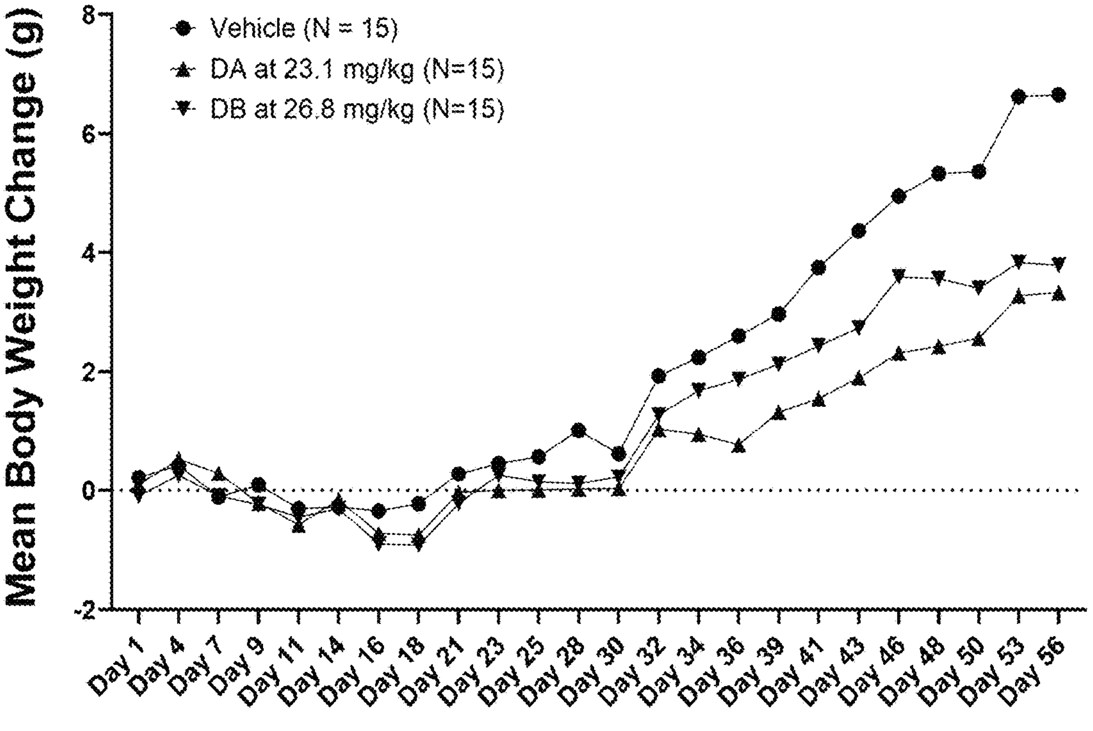
FIG. 6 shows mean absolute body weight change during 56-day treatment period in DIO mice from Example 6.

The mean absolute body weight change (in grams) and normalized body weight change (% of baseline) during 56-day treatment period of the three treatment groups are presented in FIG. 6 and Table 6.

TABLE 6

Mean normalized body weight change (% of baseline) during 56-day treatment period in DIO mice

| Group | Mean normalized body weight (% of baseline) on indicated study days 0 | 106.7 | 4 | 7 | 9 | 11 | 14 | 16 | 18 | 21 | 23 | 25 |
|---|---|---|---|---|---|---|---|---|---|---|---|---|
| DA 23.1 mg/kg | 100.0 | 108.4 | 101.1 | 100.6 | 99.5 | 98.8 | 99.6 | 98.5 | 98.4 | 99.9 | 99.9 | 100.0 |
| DB 26.8 mg/kg | 100.0 | 114.2 | 100.5 | 99.7 | 99.4 | 99.0 | 99.3 | 98.0 | 97.9 | 99.5 | 100.5 | 100.3 |
| Vehicle | 100.0 | 100.4 | 100.9 | 99.7 | 100.1 | 99.3 | 99.3 | 99.1 | 99.4 | 100.5 | 100.8 | 101.1 |

TABLE 6-continued

Mean normalized body weight change (% of baseline) during 56-day treatment period in DIO mice

| Group | Mean normalized body weight (% of baseline) on indicated study days 28 | 30 | 32 | 34 | 36 | 39 | 41 | 46 | 49 | 51 | 53 | 56 |
|---|---|---|---|---|---|---|---|---|---|---|---|---|
| DA 23.1 mg/kg | 100.0 | 100.0 | 102.0 | 101.9 | 101.5 | 102.6 | 103.1 | 103.9 | 104.7 | 104.9 | 105.2 | 106.7 |
| DB 26.8 mg/kg | 100.2 | 100.5 | 102.8 | 103.6 | 104.1 | 104.7 | 105.3 | 106.0 | 107.8 | 107.8 | 107.4 | 108.4 |
| Vehicle | 102.0 | 101.2 | 104.0 | 104.7 | 105.5 | 106.2 | 107.9 | 109.2 | 110.5 | 111.3 | 111.4 | 114.2 |

Feeding with high-fat diet induced body weight gain in all three experimental groups. However, treatment with 26.8 mg/kg of DB or 23.1 mg/kg of DA led to less body weight gain as compared to vehicle treatment. Particularly, through Day 34 to Day 56, body weight gain was less in animals treated with 23.1 mg/kg of DA than in those treated with 26.8 mg/kg of DB. Based on these data, DA has a stronger efficacy than DB not only in food intake reduction but also in body weight control on the basis of a different anion for the salt.

EXAMPLE 7

This example shows the maximum tolerated dose of two denatonium salts, denatonium benzoate (DB, molecular weight: 446.58 g/mol) that is commercially available and denatonium acetate (monohydrate) (DA, molecular weight (MW): 402.53 g/mol) that Aardvark Therapeutics had synthesized under GMP conditions pursuant to a supply contract. The drugs were administered to Sprague Dawley rats with a 14-day observational period. Twenty-four Male Sprague Dawley (SD) rats and 24 female SD rats were purchased from Envigo at 8-10 weeks of age. The DA group had four dose levels (120, 360, 1000, and 2000 mg/kg, single administration by oral gavage), 3 rats per sex, 6 animals in total per dose level; and the DB group: four dose levels (120, 360, 1000, and 2000 mg/kg, single administration by oral gavage), 3 rats per sex, 6 animals in total per dose level. The estimated median lethal dose ($LD_{50}$) was determined by a nonlinear regression [model: Y=100/(1+10^(Log EC50-X)), Hill slope=1.0) to calculate $LD_{50}$. The mortality rates at all dose levels in the two experimental groups are presented in Table

TABLE 7

Mortality rates at all dose levels of DA and DB

| Drug | Dose level (mg/kg) | Sex | No. of animals | No. of animals died within 24 h post dosing | Mortality rate |
|---|---|---|---|---|---|
| Denatonium Acetate | 120 | Male | 3 | 0 | 0% |
| | | Female | 3 | 0 | |
| | 360 | Male | 3 | 0 | 0% |
| | | Female | 3 | 0 | |
| | 1000 | Male | 3 | 0 | 50% |
| | | Female | 3 | 3 | |
| | 2000 | Male | 3 | 3 | 100% |
| | | Female | 3 | 3 | |
| Denatonium Benzoate | 120 | Male | 3 | 0 | 0% |
| | | Female | 3 | 0 | |
| | 360 | Male | 3 | 0 | 0% |
| | | Female | 3 | 0 | |
| | 1000 | Male | 3 | 1 | 66.7% |
| | | Female | 3 | 3 | |

TABLE 7-continued

Mortality rates at all dose levels of DA and DB

| Drug | Dose level (mg/kg) | Sex | No. of animals | No. of animals died within 24 h post dosing | Mortality rate |
|---|---|---|---|---|---|
| | 2000 | Male | 3 | 3 | 100% |
| | | Female | 3 | 3 | |

Although the MTD (maximum tolerated dose) was the same (360 mg/kg) for both DA and DB in rats, dosing with 1000 mg/kg DA resulted in lower mortality rate as compared with the same dose of DB (50% vs. 66.7%). Therefore, these data show that DA is a safer drug than DB on the basis of a different anion for the salt.

Figure 7A:
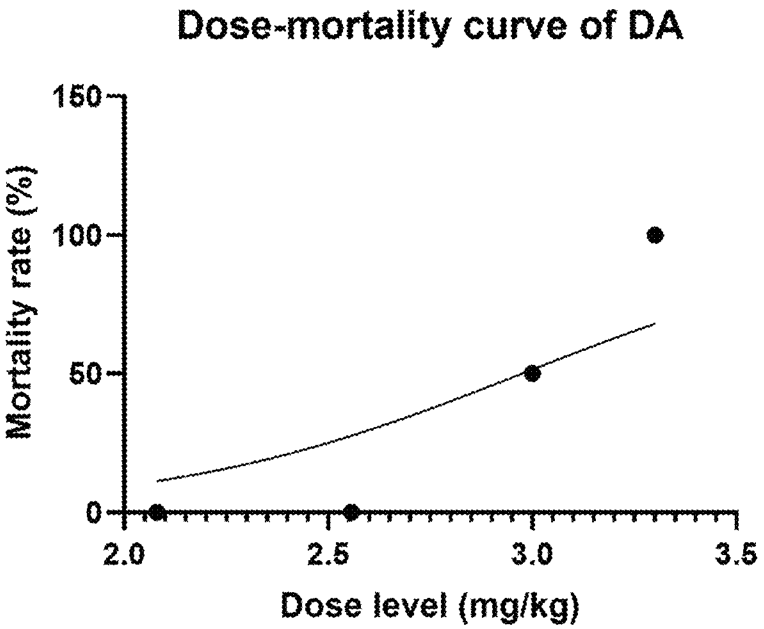
FIGS. 7A and 7B show dose-mortality curves of DA and DB from Example 7.
Figure 7B:
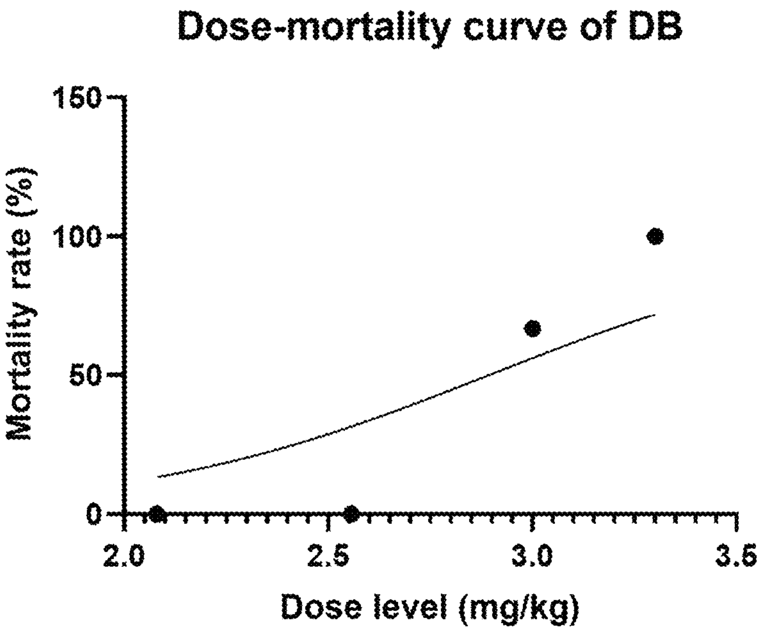

The dose-mortality curves of DA and DB are shown in FIGS. 7A and 7B. The estimated $LD_{50}$ values of DA and DB and fitting parameters are presented in Table 8. The estimated $LD_{50}$ of DA is higher than that of DB (945 mg/kg vs. 784 mg/kg) with the similar goodness-of-fit parameters.

TABLE 8

The estimated $LD_{50}$ and fitting parameters

| Drug | Estimated $LD_{50}$ | 95% CI (profile likelihood) of $LD_{50}$ | Goodness of Fit: Degrees of Freedom | Goodness of Fit: R-squared |
|---|---|---|---|---|
| Denatonium Acetate | 945 mg/kg | 149.3 to 9263 mg/kg | 3 | 0.721 |
| Denatonium Benzoate | 784 mg/kg | 111.8 to 7105 mg/kg | 3 | 0.724 |

Therefore, DA is a safer drug than DB on the basis of a different anion for the salt.

EXAMPLE 8

This example provides an immediate release 50 mg granule formulation of denatonium acetate monohydrate (DA) as a free base as an immediate gastric release oral pharmaceutical formulation.

Table 9 shows qualitative and quantitative formulation composition of DA.

| Ingredient | Quality Standard | Function | Quantity (%) w/w | DA capsule-50 mg (mg/cap) | Limits based on IID: Max Potency for Unit Dose (mg) | Reference |
|---|---|---|---|---|---|---|
| Denatonium acetate monohydrate | In-house | API | 23.55 | 59.03 (20 mg Denatonium base) | N/A | N/A |
| Povidone (KOLLIDON 30) | USP | Binder | 2.36 | 5.90 | 61.5 | Oral - Capsule |
| Sugar Spheres (VIVAPHARM ® Sugar Spheres 35-45) | NF | Substrate | 68.85 | 172.57 | 314.13 | Oral - Capsule |
| Hypromellose (Methocel E5 Premium LV Hydroxypropyl Methylcellulose) | USP | Binder | 3.64 | 9.14 | 150 | Oral - Capsule |
| Talc (MicroTalc MP 1538 USP Talc) | USP | Anti-tacking agent | 1.09 | 2.74 | 14 | Oral - Capsule, coated pellets |
| Talc (extra granular) (MicroTalc MP 1538 USP Talc) | USP | Flow aid | 0.50 | 1.25 | 284.38 | Oral - Capsule |
| Total weight of beads | | | 250.62 | | N/A | N/A |
| Hard Gelatin Capsule Shells; Cap: White Opaque: Body: White Opaque; Size: 1 | USP | Capsule shell | N/A | 73.3 | 107 | Oral - Capsule |
| Total weight of Filled Capsule | | | | 323.9 | N/A | N/A |

IID, the Inactive Ingredient Database;
API, active pharmaceutical ingredient;
USP, the US Pharmacopeia;
NF, the National Formulary
* Solvents such as Ethyl Alcohol USP 190 Proof (190 Proof Pure Ethyl Alcohol) and purified water (USP) were used for the preparation of drug solution and seal coating dispersion, but are removed during the manufacturing process.

Figure 8:
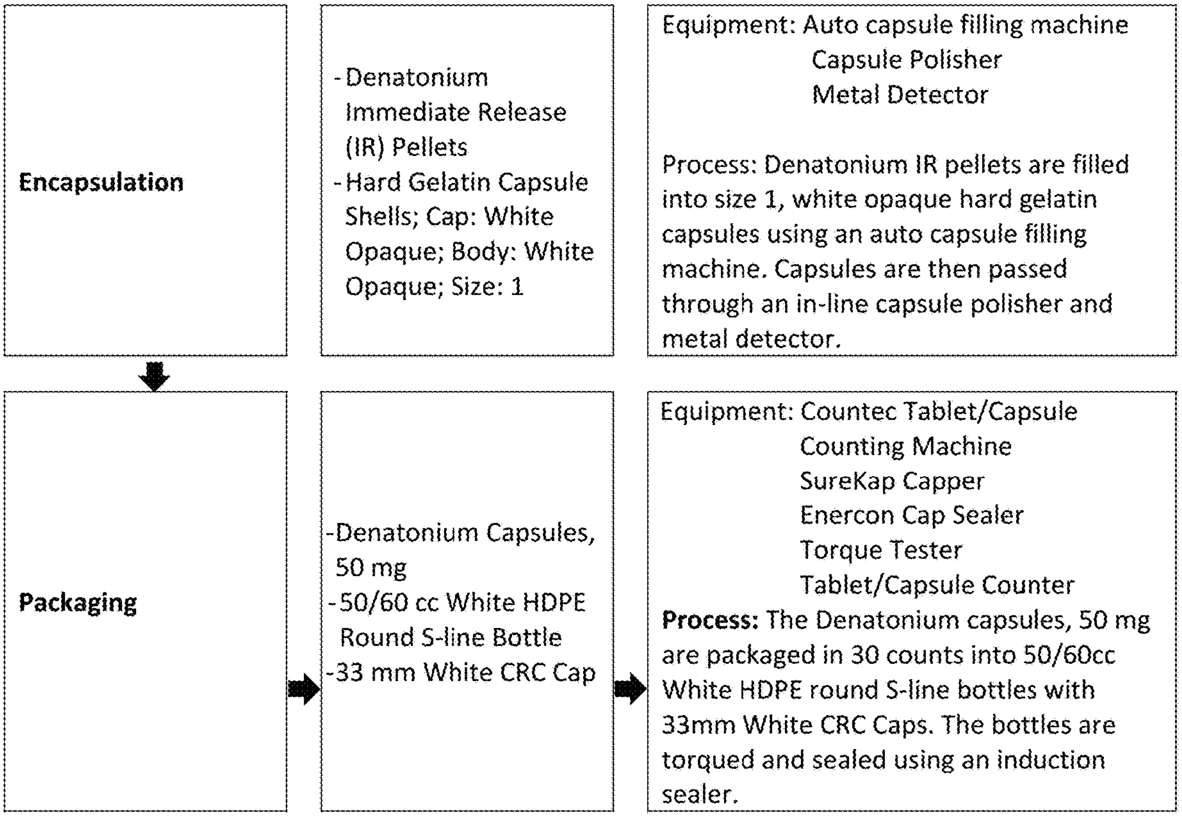
FIG. 8 shows a drug product/formulation flow diagram.

A schematic of the formulation process is shown in FIG. 8.

The detailed manufacturing steps are described below.

1. Drug Layering Process—Drug Layered Pellets

Drug layering process was performed in a Fluid bed granulator equipped with the rotor insert (rotor granulator). Drug solution was prepared by solubilizing Povidone K30 (Kollidon 30) and Denatonium Acetate in ethyl alcohol. The drug solution was sprayed tangentially on to the bed of sugar spheres (35/45 mesh) moving in a circular motion in the rotor granulator. The final drug loaded pellets were then dried for ten (10) minutes in the rotor granulator, discharged and screened through a #20 mesh.

2. Seal Coating Process—Seal Coated Pellets

Seal coating dispersion was prepared by separately dissolving Hypromellose E5 in a mixture (1:1) of ethyl alcohol and purified water until a clear solution was obtained. The remaining quantity of ethyl alcohol was then added to the above solution followed by talc. The dispersion was mixed for 20 minutes to allow for uniform dispersion of talc. The seal coating dispersion was sprayed tangentially on to the drug loaded pellets to achieve 5% weight gain. The seal coated pellets were then dried for five (5) minutes in the rotor granulator, discharged and dried further in a tray dryer/oven at 55° C. for 2 hours. The seal coated pellets were then screened through a #20 mesh.

3. Final Blending—Denatonium Immediate Release (IR) Pellets

The seal coated pellets were blended with talc screened through mesh #60 using a V-Blender for ten (10) minutes and discharged. The blended seal coated beads, Denatonium IR Pellets, were used for encapsulation.

4. Encapsulation—Denatonium Capsules, 50 mg

The Denatonium IR pellets, 50 mg, were filled into size 1, white opaque hard gelatin capsules using an auto capsule filling machine. Capsules were then passed through an in-line capsule polisher and metal detector. In-process controls for capsule weight and appearance was performed during the encapsulation process. Acceptable quality limit (AQL) sampling and testing was performed by Quality Assurance (QA) on a composite sample during the encapsulation process. Finished product composite sample was collected and analyzed as per specification for release testing.

5. Packaging—Capsules, 50 mg—30 Counts

The 50 mg capsules were packaged in 30 counts into 50/60 cc White HDPE round S-line bottles with 33 mm White CRC Caps. The bottles were torqued and sealed using an induction sealer.

We claim:

1. A method for effecting weight loss, comprising administering to a subject in need thereof an oral pharmaceutical formulation, wherein the oral pharmaceutical formulation comprises: (i) a bitter agonist comprising a denatonium salt, wherein the denatonium salt comprises a sour anion; (ii) a coating or capsule; and (iii) from about 0.5 g to about 5 g acetic acid.

2. The method of claim 1, wherein the oral pharmaceutical formulation comprises talc, a cellulose, or a saccharide.

3. The method of claim 1, wherein the oral pharmaceutical formulation further comprises an organic acid selected from malic acid, maleic acid, and citric acid, and combinations thereof.

4. The method of claim 1, wherein the subject is an adult and the denatonium salt is administered at a daily dosage of from about 10 mg to about 600 mg.

5. The method of claim 4, wherein the daily dosage of the denatonium salt is from about 10 mg to about 200 mg.

6. The method of claim 5, wherein the daily dosage of the denatonium salt is from about 10 mg to about 100 mg.

7. The method of claim 1, wherein the denatonium salt is denatonium acetate (DA).

8. The method of claim 7, wherein the subject is an adult and the DA is administered at a daily dosage of from about 10 mg to about 200 mg.

9. The method of claim 1, wherein the subject is an adult and the denatonium salt is administered at a daily dosage of from about 5 mg/kg to about 50 mg/kg body weight per day.

10. The method of claim 1, wherein the subject is an adult and the denatonium salt is administered at a daily dosage to achieve a concentration in the GI tract of from about 10 parts per billion to about 10 ppm.

11. The method of claim 7, wherein the subject is an adult and the DA is administered at a daily dosage of from about 10 mg to about 600 mg.

12. The method of claim 7, wherein the subject is an adult and the DA is administered at a daily dosage of from about 0.01 wt % to about 10 wt %.

13. The method of claim 7, wherein the subject is an adult and the DA is administered once per day, twice per day, or three times per day.

14. The method of claim 1, wherein the subject is obese.

15. The method of claim 14, wherein the denatonium salt is denatonium acetate (DA).

16. The method of claim 15, wherein the DA is administered at a daily dosage of from about 10 mg to about 600 mg.

* * * * *